US008987229B2

(12) United States Patent
Boulat et al.

(10) Patent No.: US 8,987,229 B2
(45) Date of Patent: Mar. 24, 2015

(54) SEMI-FLUID FOOD PRODUCT COMPRISING BETA-GLUCAN FIBRES

(75) Inventors: Céline Boulat, Saint Chenon (FR); Olivier Noble, Orsay (FR); Laurent Schmitt, Igny (FR); Fabien Vauloup, Massy (FR)

(73) Assignee: Compagnie Cervais Danone, Paris (FR)

( * ) Notice: Subject to any disclaimer, the term of this patent is extended or adjusted under 35 U.S.C. 154(b) by 659 days.

(21) Appl. No.: 12/527,542

(22) PCT Filed: Feb. 19, 2008

(86) PCT No.: PCT/EP2008/052001
§ 371 (c)(1),
(2), (4) Date: Aug. 17, 2009

(87) PCT Pub. No.: WO2008/101924
PCT Pub. Date: Aug. 28, 2008

(65) Prior Publication Data
US 2010/0056471 A1    Mar. 4, 2010

(30) Foreign Application Priority Data

Feb. 20, 2007 (FR) ..................................... 07 53385

(51) Int. Cl.
| A61K 31/715 | (2006.01) |
| A23L 1/308 | (2006.01) |
| A23L 1/09 | (2006.01) |
| A23L 1/052 | (2006.01) |
| C08B 37/00 | (2006.01) |
| C08L 3/02 | (2006.01) |
| C08L 5/00 | (2006.01) |
| A23C 9/137 | (2006.01) |
| A23L 1/10 | (2006.01) |
| A23L 2/52 | (2006.01) |

(52) U.S. Cl.
CPC .................. *A23L 1/3082* (2013.01); *C08L 5/00* (2013.01); *C08L 3/02* (2013.01); *C08B 37/0024* (2013.01); *A23C 9/137* (2013.01); *A23L 1/095* (2013.01); *A23L 1/1016* (2013.01); *A23L 2/52* (2013.01); *A23V 2002/00* (2013.01); *A23V 2250/5116* (2013.01)
USPC .......................................................... 514/54

(58) Field of Classification Search
None
See application file for complete search history.

(56) References Cited

U.S. PATENT DOCUMENTS

| 2004/0258829 A1 | 12/2004 | Zheng et al. |
| 2004/0266725 A1* | 12/2004 | Inohara et al. ................. 514/54 |
| 2005/0271613 A1 | 12/2005 | Suzuki et al. |

FOREIGN PATENT DOCUMENTS

| EP | 0432835 | * | 6/1991 |
| EP | 0 898 900 | | 3/1999 |
| WO | WO 00/67592 | | 11/2000 |
| WO | WO 02/082929 | | 10/2002 |
| WO | WO 2005/039300 | * | 5/2005 |
| WO | WO 2006/040395 | | 4/2006 |

OTHER PUBLICATIONS

Ohkuma, K. et al "Fibersol-2: a soluble, non-digestible, starch-derived dietary fibre" Chapter 44 in Advanced Dietary Fibre Technology (2000) McCleary, B. & Prosky, L. (eds.) Blackwell Science Ltd., Oxford, UK.*
Yamatoya, K. et al "Effects of hydrolyzed guar gum on cholesterol . . . " Food Hydrocolloids (1997) vol. 11, No. 2, pp. 239-242.*
Floury, J. et al "Effect of high pressure homogenisation on methylcellulose . . . " J. Food Eng. (2003) vol. 58, pp. 227-238.*
Norton, I. et al "A molecular model for the formation and properties of fluid gels" Int. J. Biol. Macromol. (1999) vol. 26, pp. 255-261.*
International Search Report dated Apr. 7, 2008, for International Application No. PCT/EP2008/052001.

* cited by examiner

*Primary Examiner* — Leigh Maier
(74) *Attorney, Agent, or Firm* — Finnegan, Henderson, Farabow, Garrett & Dunner LLP

(57) ABSTRACT

The present invention relates to a semi-fluid thermized aqueous solution comprising β-glucan fibers and a sufficient amount of at least one viscosity depressant chosen from the group composed of maltodextrins having a maximum DE of 18, at least partially hydrolyzed guar gum, inulin and fructooligosaccharides. Another subject of the invention is a process for preparing such a thermized aqueous solution comprising a step of slowly cooling a thermized dispersion comprising water, at least one viscosity depressant and β-glucan fibers, under shear. The invention lastly relates to the use of such a thermized aqueous solution in a food product.

12 Claims, 1 Drawing Sheet

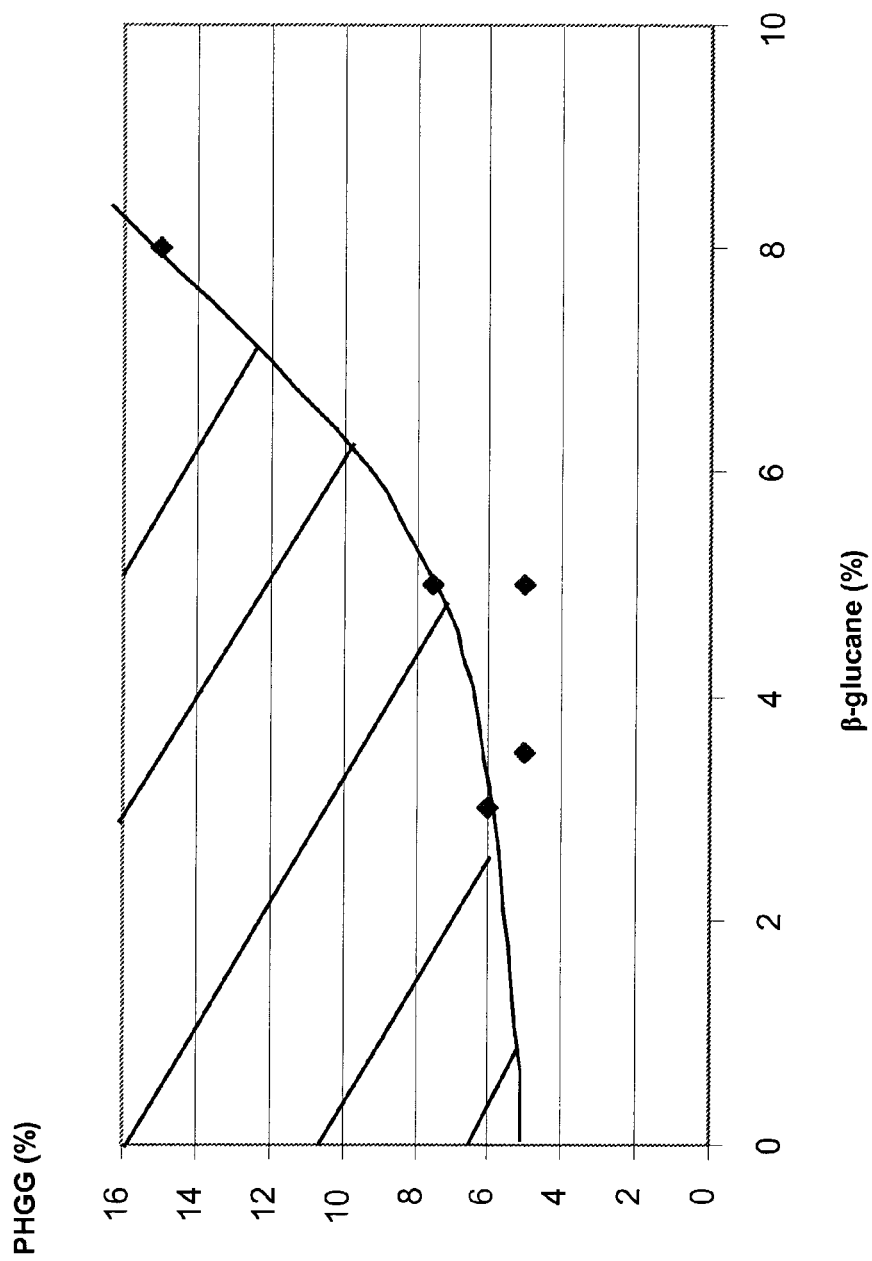

SEMI-FLUID FOOD PRODUCT COMPRISING BETA-GLUCAN FIBRES

The objective of the invention is the incorporation of β-glucan fibres in dairy products.

β-glucan fibres extracted from cereals are known for their health benefits. In particular:
- they can reduce blood cholesterol levels on and after a dose of 0.75 g of β-glucan,
- they can also bring a reduction in postprandial insulin levels (insulinaemic response) at doses in the order of 4 g with a potential benefit on weight management.

Oat or barley extracts enriched with β-glucan, having β-glucan levels of between 20% and 50% are commercially available. However, these products remain difficult to use in fresh dairy products, notably on account of the high doses to be incorporated and the strong cereal taste that is generated.

A purified extract of barley β-glucan having a β-glucan content of more than 70% is proposed by Cargill under the trade name Barliv. This product has a much more neutral taste but it remains difficult to incorporate in fermented dairy products.

Also, the addition of β-glucan fibres in the dairy mix before fermentation disturbs the formation of lactic gel and, after fermentation, a poor quality whey is obtained with substantial phase difference.

Further, the incorporation of high quantities of this extract in an aqueous preparation, a fruit preparation for example, leads to obtaining a highly textured preparation which, in addition, gels on storage after a few hours.

Heat treatment of the aqueous preparation adds a further difficulty for incorporation of this ingredient.

Processes which facilitate the incorporation of texturing fibres (i.e. which induce increased viscosity of the medium to which they are added) into dairy products are already known. For example, international application WO 00/67592 teaches the addition of a viscosity lowering compound (maltodextrin, hydrolysed guar gum, inulin) to a composition containing glucomannan.

However, in addition to a strong texturizing property, β-glucan fibres also have a strong gelling property. Yet, the mere addition of a viscosity lowering compound does not prevent gelling (setting) induced by β-glucan fibres.

Up until to the present time, to provide consumers simultaneously with a dairy product and β-glucan fibres, dual-compartment products have been proposed: one compartment containing the dairy product and another compartment containing flakes rich in β-glucan fibres to be added to the dairy product before consumption. In addition to the high cost of said dual-compartment products, the organoleptic results are not satisfactory. The flakes are either too hard if the mixed product is consumed immediately, or are pasty if consumed some time later.

The preparation of fermented dairy products containing significant doses of β-glucan, and sensorially acceptable, therefore raises difficulties which to date have not been overcome.

In unexpected manner the inventors have shown that it is possible to prepare a semi-fluid, thermised aqueous solution containing a significant quantity of β-glucan fibres, through the addition of a viscosity lowering compound combined with the use of a slow cooling process under shear.

One first subject-matter of the invention is therefore a semi-fluid, thermised aqueous solution containing β-glucan fibres, characterized in that it contains:
a. 3% to 12% by weight, relative to the total weight of the solution, of said β-glucan fibres, and
b. a sufficient quantity, between 5% and 30% by weight relative to the total weight of the solution, of at least one viscosity lowering compound chosen from the group consisting of maltodextrins having a maximum DE of 18, at least partly hydrolysed guar gum, inulin and fructo-oligosaccharides (FOS).

Under the present invention, the chosen viscosity lowering compound is preferably at least partly hydrolysed guar gum.

By "thermised" is meant "treated thermally to remove microbiological contaminants". This treatment may be pasteurization, sterilization or any other thermal process.

By "semi-fluid" is meant a solution which has a viscosity (measured at 10° C.) of less than 10,000 mPa·s.

β-glucan fibres are soluble food fibres which are found in cereals, in barley and oats in particular. β-glucan fibres can also be extracted from the cell wall of green plants and from some algae and fungi (maitake and shiitake). Under the scope of the invention, the β-glucan fibres are intact fibres i.e. the fibres are not previously modified by chemical or enzymatic treatment such as the use of exogenous cellulases. The intact β-glucan fibres most often have a molecular weight in the order of 220,000 Da±10,000 Da (molecular weight measured by gel permeation chromatography).

The source of β-glucan fibres is most often an oat or barley extract rich in said fibres. Said extracts are commercially available. In particular Cargill markets a purified extract of barley β-glucan having a β-glucan content of more than 70% (under the trade name Barliv™).

Maltodextrins are products obtained by hydrolysis of starch. Under the present invention, maltodextrins are used having a hydrolysis degree (DE) of less than 18. The inventors have effectively found that only weakly hydrolysed maltodextrins are able to reduce the viscosity of the aqueous solution and to prevent its gelling.

The degree of hydrolysis characterizes the degree of polymerization of maltodextrins: maltodextrins with low DE are weakly hydrolysed maltodextrins, also called long chain maltodextrins.

Under the scope of the present invention, the maltodextrins advantageously have a DE of less than 10, more advantageously less than 6.

Under the present invention, the at least partly hydrolysed guar gum advantageously has a molecular weight of between 10,000 and 100,000 Da, more advantageously between 10,000 and 50,000 Da, and further advantageously between 10,000 and 30,000 Da. In particular, the at least partly hydrolysed guar gum may have a molecular weight of around 20,000 Da.

This at least partly hydrolysed guar gum is advantageously obtained after enzymatic hydrolysis of guar gum.

Inulins are natural oligosaccharides (chiefly of plant origin) containing fructose units. They are mainly found in chicory (chief source of products currently on the market), onions, leeks, garlic, bananas, asparagus and artichokes.

Under the present invention, inulins advantageously have a molecular weight of between 1,000 and 5,000 Da.

The term fructo-oligosaccharides (FOS) refers to small chain oligosaccharides containing D-fructose and D-glucose units, conventionally containing 3 to 5 monosaccharide units.

Under the present invention, the fructo-oligosaccharides advantageously have a molecular weight of between 500 and 1,000 Da.

All these viscosity lowering compounds are soluble compounds with low texturing properties. In particular, it is found that their molecular weight is advantageously less than 50,000 Da, more advantageously less than 30,000 Da. These viscosity lowering compounds all have the capacity of forming a continuous phase of reasonable viscosity (limited). The β-glucan fibres form a dispersed phase which will integrate the continuous phase.

Under the present invention, the expression "low texturing property" means that the viscosity lowering compounds have a viscosity at 10% of less than 1,000 mPa·s.

As viscosity lowering compound, preference is given to at least partly hydrolysed guar gum which does not give rise to any tolerance problems and is low in calories, unlike maltodextrins whose calorie content may be considered to be too high in some applications, and unlike inulins which may give rise to problems of digestive tolerance.

The content of β-glucan fibres in the aqueous solution of the invention varies from 3% to 12% by weight relative to the total weight of said solution. Contents of less than 3% by weight would provide little food benefit. Also, an aqueous solution containing more than 12% by weight β-glucan fibres is difficult to obtain.

The β-glucan fibre content in the aqueous solution of the invention advantageously varies between 3% and 10% by weight, more advantageously between 3% and 8%, further advantageously between 3% and 7% by weight and even further advantageously between 3% and 6.5% by weight relative to the total weight of said solution. However, very satisfactory results can also be obtained with high β-glucan fibre contents i.e. in the order of 8 to 10% by weight relative to the total weight of said solution (cf. Examples 4 and 6).

The content of viscosity lowering compound in the aqueous solution of the invention varies from 5% to 30% by weight, relative to the total weight of said solution.

The content of viscosity lowering compound depends firstly on the β-glucan fibre content and secondly on the cooling rate kinetics in the process used.

The higher the content of β-glucan fibres in the solution, the greater the quantity of viscosity lowering compound which must be added. In parallel, the slower the cooling kinetics in the manufacturing process, the lesser the amount of viscosity lowering compound which needs to be added.

One method to determine the minimum content of viscosity lowering compound to be added is explained in Example 3.

According to one advantageous variant of the invention, the aqueous solution contains 3% to 5% by weight of said β-glucan fibres, and 5% to 20% more advantageously 8% to 15% by weight of said viscosity lowering compound, relative to the total weight of the solution.

According to one advantageous variant of the invention, the aqueous solution contains 5% to 8% by weight of said β-glucan fibres, and 7% to 20% more advantageously 12% to 15% by weight of said viscosity lowering compound, relative to the total weight of the solution.

According to another advantageous variant of the invention, the aqueous solution contains 8% to 12%, advantageously 8% to 10% by weight of said β-glucan fibres, and 10% to 30% by weight of said viscosity lowering compound relative to the total weight of the solution.

The indicated contents of viscosity lowering compound correspond to the contents necessary for the macromolecular compounds to play their viscosity lowering role. Greater quantities thereof could be added. For example, contents of more than 30% by weight of at least partly hydrolysed guar gum could be added, which would then firstly play its role as viscosity lowering compound and secondly would provide fibres to the end product.

The aqueous solution of the invention may further contain a fruit juice concentrate, concentrated fruit purée and/or fruit pieces.

A further subject of the invention is a process to prepare a thermised aqueous solution according to the invention.

This process comprises a slow cooling step of a thermised dispersion containing:
water,
at least one viscosity lowering compound, and
β-glucan fibres,
under shear, down to a temperature of between 4° C. and 30° C.

In particular, this process comprises the following successive steps:
a. Dispersing the viscosity lowering compound and β-glucan fibres in water;
b. Heating the dispersion obtained after the preceding step up to a holding temperature and maintaining this dispersion at said holding temperature;
c. Slow cooling of the dispersion obtained after step b), under shear, down to a temperature of between 4° C. and 30° C.

The inventors have found that, in addition to the adding of a viscosity lowering compound, the slow cooling step under shear is essential for addition of the β-glucan fibres to an aqueous solution, to avoid both a too large increase in viscosity and setting (gelling). In the event of sudden cooling, it is effectively ascertained that gelling of the solution occurs. This is also observed if cooling is static (i.e. with no shear).

Dispersions having viscosity values of more than 10,000 mPa·s raise significant pumping problems. Under the scope of the present invention, a semi-fluid dispersion is a dispersion which has a viscosity (measured at 10° C.) of less than 10,000 mPa·s.

Cooling is advantageously conducted at a maximum rate of 2° C./min.

For a fixed content of viscosity lowering compound, the slower the kinetics of cooling, the higher the content of β-glucan fibres which can be added.

From an economic viewpoint, it is difficult to contemplate cooling which lasts for more than one day. Cooling is therefore advantageously conducted at a rate of between 0.15° C./min and 1° C./min.

During cooling, the shear rate generally lies between 10 s$^{-1}$ and 800 s$^{-1}$ advantageously between 50 s$^{-1}$ and 500 s$^{-1}$, and more advantageously between 50 s$^{-1}$ and 300 s$^{-1}$. It would appear that shear rate only has a small impact on viscosity and on setting of the semi-fluid aqueous solution obtained. Shear during cooling is absolutely necessary however.

Thermisation conditions correspond to those conventionally used in the food sector. The holding temperature is therefore advantageously between 80° C. and 95° C. Also the holding time advantageously varies from 2 minutes to 20 minutes.

The process may, after step a) and prior to step b), comprise a step to add a concentrate of fruit juice to the dispersion obtained, or a concentrated fruit purée or fruit pieces, and/or sugar.

During step c), the aqueous solution is cooled down to its temperature of use and/or storage. In the food sphere, a temperature of 10° C. is a conventional storage temperature.

This process does not necessitate operating conditions that are difficult to control, such as pressurized conditions. The temperatures applied are fully conventional. The process is therefore easy to apply at industrial level.

A further subject of the invention is a semi-fluid food product containing the pasteurized aqueous solution of the invention.

A semi-fluid food product is a food product having a water activity (AW) of more than 0.90. Water activity is the ratio of a product's water vapour pressure over the vapour pressure of pure water at one same temperature.

This food product advantageously contains 0.5% to 5% by weight of β-glucan fibres relative to its total weight.

This food product is advantageously chosen from among the group consisting of soy-based products, products containing fruit and/or vegetables, fillers for cereal products and dairy products.

Dairy products are notably fermented dairy products.

By "fermented dairy products" is more particularly meant fermented dairy products ready for human consumption i.e. fermented dairy foods. In the present application, those foods particularly concerned are fermented milks and yoghurts. Said fermented dairy foods may alternatively befromage blanc or petit-suisses.

The terms "fermented milks" and "yoghurts" are given their usual meaning in the dairy industry i.e. products intended for human consumption and derived from acidifying lactic fermentation of a milk substrate. These products may contain secondary ingredients such as fruit, plants, sugar etc. Reference may made for example to French Decree n° 88-1203 of 30 Dec. 1988 on fermented milks and yoghurt or yoghourt, published in the official journal of the French Republic on 31 Dec. 1988.

Reference may also be made to the "Codex Alimentarius" (prepared by the Codex Alimentarius Commission under the aegis of the FAO and WHO and published by the FAO Information Division, available online at http://www.codexalimentarius.net (cf. more particularly volume 12 of the Codex Alimentarius "Codex standards for milk and milk products" and the standard "CODEX STAN-A-1 1(a)-1975").

The term "fermented milk" in the present application is therefore reserved for a milk product prepared with a milk substrate which has undergone treatment at least equivalent to pasteurization, inoculated with microorganisms belonging to the species or characteristic species of each product. A "fermented milk" has not undergone any treatment allowing extraction of a constituent element of the milk substrate used, and notably has not undergone drainage of the coagulum. The coagulation of "fermented milks" must not be obtained by means other than those resulting from the activity of the microorganisms used.

The term "yoghurt" is reserved for the fermented milk obtained according to constant local usage, through the development of specific thermophilic lactic bacteria called *Lactobacillus bulgaricus* and *Streptococcus thermophilus* which must be in the living state in the end product, to the proportion of at least 10 million bacteria per gram relative to the milk part.

In some countries, regulations authorize the addition of other lactic bacteria in the production of yoghurt, and in particular the additional use of strains of *Bifidobacterium* and/or *Lactobacillus acidophilus* and/or *Lactobacillus casei*.

These additional lactic strains are intended to impart various properties to the end product, such as the property of promoting the equilibrium of intestinal flora, or modulating the immunity system.

In practice, the term "fermented milk" is generally used to designate fermented milks other than yoghurts, and depending on countries may be given the name "Kefir", "Kumiss", "Lassi", "Dahi", "Leben", "Filmjôlk", "Villi", "Acidophilus milk" for example.

The quantity of free lactic acid contained in the fermented milk substrate must not be less than 0.6 g per 100 g at the time of sale to the consumer, and the protein content relative to the milk content must not be less than that of a normal milk.

The name "fromage blanc" or "petit-suisse" in the present application is reserved for non-ripened, non-salted cheese which has undergone fermentation by lactic bacteria alone (no fermentation other than lactic fermentation).

The dry matter content of fromages blancs can be lowered down to 15 g or 10 g per 100 g of fromage blanc depending on whether their fat content is 25% higher than 20 g, or no more than 20 g per 100 g of fromage blanc after complete desiccation. The dry matter content of a fromage blanc lies between 13% and 20%. The dry matter content of a petit-suisse is not lower than 23 g per 100 g of petit-suisse. It generally lies between 25% and 30%. Fromages blancs and petit-suisses are generally grouped together under the designation "fromages frais" conventionally used in the technical area of the present invention.

A further subject of the invention is the semi-fluid thermised aqueous solution of the invention, or the food product containing the same, as functional food.

The term "functional food" is therefore reserved in the present application for food having the capacity to influence body functions beneficially, so as to improve well-being and health and to reduce the risk of onset of disease (ILSI definition: Concepts of functional foods by M. Ashwell—2002).

In particular said functional food has the following therapeutic objectives: prevention of cardiovascular disease, of diabetes, of obesity and prevention or treatment of overweight.

Said functional food may in particular be used as part of a food diet targeting slimming or weight management.

Said solution or said food product can be used as a dietary food, in particular to reduce the blood cholesterol levels or to reduce postprandial insulin levels.

The following examples illustrate the invention.

EXAMPLE 1

Preparation of Semi-Fluid Solutions Containing 5% β-Glucan

Aqueous solutions are prepared containing 5% by weight β-glucan fibres (7.15% Barliv™) and:
No viscosity lowering compound (comparative example),
10% by wt. maltodextrin DE 6,
10% by wt. hydrolysed guar gum (PHGG).

The maltodextrin used is the reference Glucidex® (Roquette). For the hydrolysed guar, the reference used is Sunfiber® R (Taiyo Kagaku).

The tests were performed in the laboratory or in a viscometer cell under the following conditions:
dispersion of the powders (β-glucan fibres, maltodextrin, PHGG) in cold water,
heating the mix under stirring
holding for a few minutes at a temperature of 90° C. or 95° C.,
static or dynamic (under shear) cooling down to 10° C. and measurement of viscosity at a shear rate of 64 $s^{-1}$,
storage of the solution obtained at 10° C., and observation of any gelling.

As a general rule, β-glucan disperses easily under stirring in cold water. A weakly viscous solution is then obtained, whether the β-glucan is placed in solution alone or with a viscosity lowering compound. An increase in viscosity is observed at around 60° C. during heating (viscosity of 0.15 Pa·s at 60° C. and at 150 $s^{-1}$) corresponding to β-glucan hydration.

The results observed for different mixtures are summarized in Table 1 in which the cooling time was set at 120 minutes and shear at 150 s$^{-1}$.

TABLE 1

|  | Cooling | Viscosity 10° C. D0 (mPa · s) | Gelling 10° C. D + 1 |
|---|---|---|---|
| 5% β-glucan | static | 5,900 | Yes |
|  | dynamic | 5,900 | Yes |
| 5% β-glucan + | static | Gel | Yes |
| 10% maltodextrin DE 6 | dynamic | 5,450 | No |
| 5% β-glucan + | static | 2,900 | Yes |
| 10% PHGG | dynamic | 1,200 | No |

It is ascertained that the addition of 10% PHGG brings a signification decrease in the viscosity developed after heat treatment. However, this addition does not prevent gelling of the system, which occurs after a few hours on static cooling.

Solely the combination: addition of viscosity lowering compound+dynamic cooling allows the generation of solutions containing 5% β-glucan with reduced viscosity which do not gel during storage at 10° C.

Also, cooling time is a parameter which determines the final viscosity and gelling of the system.

Rapid cooling (a few tens of seconds to a few minutes) does not allow the desired result to be obtained, whereas slower cooling (a few tens of minutes to a few hours) proves to be more favourable.

Table 2, in which the measurements were performed on the 5% β-glucan+10% PHGG system at a shear rate of 150 s$^{-1}$ during cooling, summarizes these observations.

TABLE 2

| Cooling time (min) | Viscosity 10° C. D0 (mPa · s) | Gelling 10° C. D + 1 |
|---|---|---|
| 1 | 2,500 | Yes |
| 5 | 2,460 | Yes |
| 30 | 2,400 | Yes |
| 60 | 1,800 | No |
| 120 | 1,200 | No |

If cooling time is sufficiently long (more than one hour) no gelling is observed over 28 days when the solution is stored at 10° C.

EXAMPLE 2

Preparation of Semi-Fluid Solutions Containing 5.7% β-Glucan

Aqueous solutions are prepared containing 5.7% by weight β-glucan fibres (8.14% Barliv™) and 10%, 12.5% and 15% by weight of hydrolysed guar gum (PHGG; Sunfiber® R (Taiyo Kagaku)).

The ingredients are mixed together then dispersed under stirring using an impeller of deflocculating turbine type at 800 rpm for at least one hour. The mixture is heat treated in a double-jacketed tank at 95° C. for 10 minutes. Cooling is conducted under shear (around 100 s$^{-1}$) and over a period of two hours to prevent strong gelling.

The following solutions are obtained:

TABLE 3

|  | Barliv ™ | PHGG | Water | White mass/ solution |
|---|---|---|---|---|
| Solution A | 8.14% | 10% | 81.86% | 60:40 |
| Solution B | (5.7% | 12.5% | 73.3% |  |
| Solution C | β-glucan) | 15% | 68.3% |  |

None of the solutions produced re-texturizes. The solutions are stable over time, no phase separation is seen after 21 days' storage at 10° C.

Each solution is incorporated into a white mass of stirred-type (white mass/solution weight ratio of 60:40), by way of indication the viscosity of said white mass lies between 1,100 and 1,200 mPa·s. Table 4 below gives viscosity follow-up results of the end products.

TABLE 4 viscosity at 64 s$^{-1}$, 10 s of stirred yoghurts during cold storage (10° C.).

| | Viscosity at 64 s − 1 (mPa · s)/Appearance | | | |
|---|---|---|---|---|
|  | D + 1 | D + 7 | D + 14 | D + 28 |
| Solution B mixture | 1,178 Non-gelled | 1,141 Non-gelled | 1,159 Nongelled | 1,153 Non-gelled |
| Solution C mixture | 1,580 Non-gelled | 1,575 Non-gelled | 1,588 Non-gelled | 1,596 Non-gelled |

The viscosities of the end products are of great interest since once mixed the solutions do not cause any significant viscosifying of the medium, unlike guar gum when used alone. The end products are stable at D+28 and no syneresis can be seen.

EXAMPLE 3

Obtaining a Fruit Juice Preparation Containing 6.4% β-Glucan

The β-glucan and hydrolysed guar (Sunfiber® R, Taiyo Kagaku) are placed in solution by cold dispersion in water to which concentrated fruit juice is then added. The sugar in powder form and glucose syrup are then added and the solution is acidified before applying the heat treatment conditions described in Example 1. Conventional stirring systems are sufficient to disperse the ingredients.

Fruit juice-based preparations containing 9% Barliv™ i.e. 6.4% β-glucan were prepared.

The results observed are summarized in Table 5, in which the cooling time was set at 120 minutes and shear at 150 s$^{-1}$:

TABLE 5

|  | Cooling | Viscosity 10° C. D0 (mPa · s) | Gelling 10° C. D + 1 |
|---|---|---|---|
| 6.4% β-glucan + 10% PHGG | dynamic | 4,600 | No |

EXAMPLE 4

Determination of Optimal Concentrations of β-Glucan and Partly Hydrolysed Guar Gum, Allowing a Solution of the Invention to be Obtained A determined quantity of partly hydrolysed guar gum (PHGG: Sunfiber R®—Taiyo Kagaku—Fiderstadt Germany) and β-glucan fibres (Barliv™—Cargill—Minneapolis, Minn., USA) are dispersed in water. This dispersion is then heated to 95° C. and held at this temperature. The dispersion is finally slow-cooled (for 120 minutes) under shear (150 s$^{-1}$) down to 10° C.

The viscosity (measured using a PHYSICA UDS 200 rheometer—Anton Paar) of the solution obtained is measured just after production (D0) and one day after this production (D+1).

The appearance of the solution obtained is then evaluated at D+1. The point of comparison for this evaluation is the appearance of a product which has not undergone shear but which has undergone the same heat treatment.

The results obtained are given in the following Table 6:

TABLE 6

| Concentration (w/w %) | | Viscosity (mPa · s at 64 s$^{-1}$) | Appearance |
|---|---|---|---|
| β-glucan | PHGG | D0 | D + 1 |
| 3 | 6 | 1,870 | non-gelled |
| 3.5 | 5 | 2,750 | gelled |
| 5 | 5 | 7,520 | gelled |
| 5 | 7.5 | 5,750 | very slightly gelled |
| 8 | 15 | 7,530 | non-gelled |

These are also given FIG. 1, in which the content (weight %) of PHGG is given along the Y-axis and the β-glucan content (weight %) along the X-axis.

The shaded area, above the curve, corresponds to the area in which the dispersion does not gel ("non-gel" area) whereas the area below the curve corresponds to a gelling area ("gelling" area).

The curve obtained gives the minimum PHGG content that is required relative to the desired β-glucan content, for given cooling kinetics.

The minimum contents of PHGG for other cooling kinetics can easily be determined by reproducing the teaching of this Example 3 adapted to the chosen kinetics.

EXAMPLE 5

Preparation of Fermented Dairy Products Containing β-Glucan

Products of Stirred Yoghurt Type

A product close to a textured, stirred yoghurt with fruit was able to be obtained with a 50:50 mixture of a plain stirred yoghurt (of viscosity 1,050 mPa·s at 10° C.) and a solution containing 6.4% β-glucan such as described above.

The mixing operation does not give rise to any particular difficulty and can be performed using conventional mixers.

This product has a viscosity of 1,800 mPa·s at 10° C., it has acceptable organoleptic properties and it is stable after storage at 10° C. for 28 days.

125 g of this product contain a dose of 4 g of β-glucan.
Products of Stirred Yoghurt Type A product close to a more liquid, stirred fruit yoghurt was able to be obtained with a 81:19 mixture of a plain stirred yoghurt (of viscosity 1,050 mPa·s at 10° C.) and a solution containing 6.4% β-glucan such as described above.

The mixing operation does not give rise to any particular difficulty and can be performed using conventional mixers.

This product has a viscosity of 1,070 mPa·S at 10° C. and has acceptable organoleptic properties, and it is stable when stored at 10° C. for 28 days.

125 g of this product contain a dose of 1.5 g of β-glucan.
Fermented Milk Drinks A fruit, fermented milk drink was able to be obtained with a mixture of 88% plain, drinkable fermented milk (of viscosity 30 mPa·S) and 12% of a fruit juice preparation containing 6.4% β-glucan such as described above.

The mixing operation does not give rise to any particular difficulty and can be performed using conventional mixers.

This product has a viscosity of 280 mPa·s at 10° C. and has acceptable sensorial properties, and it is stable when stored at 10° C. for 28 days.

100 g of this drink contain a dose of 0.75 g β-glucan.

EXAMPLE 6

Preparation of Semi-Fluid Solutions Containing 9.31% β-Glucan

Aqueous solutions are prepared containing 9.31% by weight of β-glucan fibres (8.14% Barliv™) and 20% by weight of hydrolysed guar gum (PHGG; Sunfiber® R (Taiyo Kagaku)).

The ingredients are mixed together then dispersed under stirring using an impeller of deflocculating turbine type, at 800 rpm for at least one hour. The mixture is heat treated in a double jacketed tank at 95° C. for 10 minutes. Cooling is conducted under shear (around 100 s$^{-1}$) and over a period of two hours to prevent strong gelling.

The following solutions are obtained:

TABLE 7

| | Barliv ™ | PHGG | Water | White mass/ solution |
|---|---|---|---|---|
| Solution D | 13.3% (9.31% β-glucan) | 20% | 66.7 | 70:30 |

This solution does not re-texturize. It is stable over time, no phase separation is observed after 21 days' storage at 10° C.

This solution is incorporated into a white mass of stirred type (weight ratio of white mass/solution 70:30), by way of indication the viscosity of said white mass lies between 1,100 and 1,200 mPa·s. Table 8 below shows the follow-up results for the viscosity of the end products.

TABLE 8

| Viscosity at 64 s$^{-1}$, 10 s of stirred yoghurts during cold storage (10° C.) | | | | |
|---|---|---|---|---|
| | Viscosity at 64 s$^{-1}$ (mPa · s) | | | |
| | D + 1 | D + 7 | D + 14 | D + 28 |
| Solution D mixture | 1,604 Non-gelled | 1,571 Non-gelled | 1,064 Non-gelled | 1,598 Non-gelled |

The viscosities of the end products are of great interest since once mixed the solution does not significantly viscosify the medium, unlike guar gum used alone. The end products are stable at D+28, no syneresis is observed. This solution D also allows the use of a substantial content (70% by weight) of white mass.

The invention claimed is:

1. A process to prepare a semi-fluid thermised aqueous solution containing β-glucan fibres that does not gel when stored at 10° C. for one day or more wherein:

the solution comprises
- a. about 5% to about 8% by weight, relative to the total weight of the solution, of said β-glucan fibres, and
- b. about 7% to about 20% by weight, relative to the total weight of the solution, of at least one viscosity lowering compound chosen from maltodextrins having a maximum DE of 18 and at least partly hydrolysed guar gum; and the process comprises a slow cooling step of a thermised dispersion containing water, at least one viscosity lowering compound, and β-glucan fibres, under shear, down to a temperature of between 4° C. and 30° C.;

wherein the slow cooling step is conducted at a maximum rate of 2° C./min and lasts at least 60 minutes;

wherein the thermised dispersion is a dispersion treated thermally to reduce the viability of microbial contaminants and/or kill microbial contaminants; and wherein the cooling under shear decreases the viscosity of the semi-fluid thermised aqueous solution.

2. The process according to claim 1, comprising the following successive steps:
- a. dispersing the viscosity lowering compound and β-glucan fibres in water;
- b. heating the dispersion obtained after the preceding step up to a holding temperature, and holding said dispersion at said holding temperature for a holding time;
- c. slow cooling of the dispersion obtained after step b), under shear, down to a temperature of between 4° C. and 30° C.

3. The process according to claim 1, wherein the shear rate, during cooling, lies between $10\ s^{-1}$ and $800\ s^{-1}$.

4. The process according to claim 2, wherein the holding temperature lies between 80° C. and 95° C.

5. The process according to claim 2, wherein the holding time varies between 2 minutes and 20 minutes.

6. The process according to claim 2, which after step a) and prior to step b), comprises adding to the dispersion concentrate of fruit juice, concentrated fruit puree, fruit pieces, and/or sugar.

7. A process for preparation of a semi-fluid food product comprising: preparing a semi-fluid thermised aqueous solution containing β-glucan fibres that does not gel when stored at 10° C. for one day or more, wherein the solution comprises
- a. about 5% to about 8% by weight, relative to the total weight of the solution, of said β-glucan fibres, and
- b. about 7% to about 20% by weight, relative to the total weight of the solution, of at least one viscosity lowering compound chosen from maltodextrins having a maximum DE of 18 and at least partly hydrolysed guar gum.

8. The process according to claim 7, wherein the food product contains 0.5% to 5% by weight β-glucan fibres, relative to its total weight.

9. The process according to claim 7, wherein the food product is chosen from soy-based products, fruit and/or vegetable-based products, fillers for cereal products, and dairy products.

10. The process according to claim 1, wherein the cooling rate is of between 0.15° C./min and 1° C./min.

11. The process according to claim 3, wherein the shear rate lies between $50^{s-1}$ and $300^{s-1}$.

12. The process according to claim 1, wherein the semi-fluid thermised aqueous solution containing β-glucan fibres does not gel when stored at 10° C. for up to 28 days.

* * * * *